(12) United States Patent
Zachmann et al.

(10) Patent No.: US 9,086,156 B2
(45) Date of Patent: Jul. 21, 2015

(54) ANALYTICAL DEVICE FOR AUTOMATED DETERMINING OF A MEASURED VARIABLE OF A MEASURED LIQUID

(75) Inventors: Tobias Zachmann, Stuttgart (DE); Ulrich Kathe, Leonberg (DE); Thomas Schipolowski, Stuttgart (DE); Ralf Bernhard, Stuttgart (DE); Christian Hirn, Ditzingen (DE); Ralf Steuerwald, Eberdingen (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 358 days.

(21) Appl. No.: 13/469,166

(22) Filed: May 11, 2012

(65) Prior Publication Data

US 2012/0285224 A1 Nov. 15, 2012

Related U.S. Application Data

(60) Provisional application No. 61/484,771, filed on May 11, 2011.

(30) Foreign Application Priority Data

May 12, 2011 (DE) .......................... 10 2011 075 762

(51) Int. Cl.
*F16K 7/16* (2006.01)
*G01N 35/10* (2006.01)
*G01N 35/08* (2006.01)

(52) U.S. Cl.
CPC *F16K 7/16* (2013.01); *G01N 35/08* (2013.01); *G01N 35/1097* (2013.01)

(58) Field of Classification Search
CPC ............. F16K 1/00; F16K 7/16; G01N 35/08; G01N 35/1097; G01N 1/38; G01N 35/1016; B67C 3/206; B67C 3/28; F04B 13/00
USPC .............. 73/64.56; 137/625.4, 607; 251/89.5, 251/209
See application file for complete search history.

(56) References Cited

U.S. PATENT DOCUMENTS 3,607,092 A * 9/1971 Neff et al. ................. 137/565.23
8,163,535 B2 * 4/2012 Reed et al. ................. 435/283.1
(Continued)

FOREIGN PATENT DOCUMENTS

| CN | 1629623 A | 6/2005 |
| DE | 7921875 | 7/1979 |

(Continued)

OTHER PUBLICATIONS

English Machine Translation of DE102009029305 to Kathe et al. pub. Mar. 10, 2011.*

*Primary Examiner* — Lisa Caputo
*Assistant Examiner* — Philip Cotey
(74) *Attorney, Agent, or Firm* — Bacon & Thomas, PLLC (57) ABSTRACT

An analytical device for automated determining of a measured variable of a measured liquid, including: a measuring cell; a measuring transducer; a control unit; a system of liquid lines; a first liquid container which is connected to the measuring cell via a first liquid path; a second liquid container, which is connected to the measuring cell via a second liquid path, liquid path can be blocked by means of at least a second valve; wherein a first pump is associated with the first liquid container; and wherein a second pump (different from the first pump) for transport of liquid along the second liquid path is associated with the second liquid container; and wherein the analytical device has a central valve switching mechanism, especially controllable by the control unit, for actuating the first valve and the second valve.

21 Claims, 3 Drawing Sheets

(56) References Cited

U.S. PATENT DOCUMENTS

| | | | |
|---|---|---|---|
| 8,201,711 B2* | 6/2012 | Tsai | 251/209 |
| 2002/0064880 A1* | 5/2002 | Merten et al. | 436/43 |
| 2006/0104827 A1* | 5/2006 | Shaw et al. | 417/245 |
| 2006/0127237 A1* | 6/2006 | Shaw et al. | 417/313 |
| 2006/0228807 A1* | 10/2006 | Nagai et al. | 436/164 |
| 2006/0239861 A1* | 10/2006 | Higashino et al. | 422/100 |
| 2007/0062583 A1* | 3/2007 | Cox et al. | 137/565.11 |
| 2008/0274539 A1 | 11/2008 | Ahluwalia et al. | |
| 2010/0197512 A1* | 8/2010 | Trinkle et al. | 506/7 |
| 2012/0173164 A1* | 7/2012 | Steuerwald et al. | 73/61.59 |

FOREIGN PATENT DOCUMENTS

| | | |
|---|---|---|
| DE | 102007032951 A1 | 1/2009 |
| DE | 102009029305 A1 | 3/2011 |
| EP | 2 199 762 A1 | 6/2010 |
| JP | 2005-532060 A | 10/2005 |
| WO | WO 2005/064328 A1 | 7/2005 |
| WO | WO 2011/000572 A1 | 1/2011 |
| WO | WO 2011/029698 A1 | 3/2011 |

* cited by examiner

ANALYTICAL DEVICE FOR AUTOMATED DETERMINING OF A MEASURED VARIABLE OF A MEASURED LIQUID

CROSS-REFERENCE TO RELATED APPLICATION

This application is a nonprovisional which claims the benefit of U.S. Provisional Application 61/484,771, which was filed on May 11, 2011.

TECHNICAL FIELD

The invention relates to an analytical device for automated determining of a measured variable of a measured liquid.

BACKGROUND DISCUSSION

Such analytical devices are applied, for example, in process measurements technology or in industrial measurements technology. For example, analytical devices can serve for monitoring and optimizing the cleaning effectiveness of a clarification plant, e.g. by monitoring the activation basin and the clarification plant outlet. Furthermore, analytical devices can be applied for monitoring drinking water or for monitoring the quality of food. Measured variables determined and monitored by analytical devices are, for example, an analyte content of a liquid, e.g. content of ions such as ammonium, phosphate or nitrate, biological or biochemical compounds content, e.g. hormones, or the content of microorganisms. Other measured variables, which are determined by analytical devices in process measurements technology, especially in the area of water monitoring, are e.g. the total carbon content (TOC) or chemical oxygen demand (COD).

Frequently in analytical devices, the sample to be analyzed is mixed with one or more reagents so that a chemical reaction occurs; the chemical reaction is detectable by means of physical methods, for example, through optical measurements. For example, the chemical reaction can affect color of the liquid sample or cause a color change, which is photometrically detectable.

In order to use such an analytical method in industry, it is desirable to provide an analytical device, which automatedly performs the required analytical method and requires as few interventions or maintenance measures by qualified operators as possible. Besides sufficient accuracy of measurement, the most important requirements for such an analytical device are robustness, simple operability and the assuring of sufficient occupational or environmental safety. Since the reagents used for the analysis in part cannot be readily allowed in the water system, their safe disposal likewise plays an essential role.

Semiautomatic and automatic analytical devices are known from the state of the art. These are often relatively complicated in construction and, consequently, susceptible to defects and, as a rule, can be used only by trained operating personnel. Thus, for example, DE 102 22 822 A1 and DE 102 27032 A1 describe online analyzers for analyzing measurement samples. The online analyzers are embodied, in each case, as cabinet devices, in which are arranged a control unit, reagent supply containers, pumps for conveying and dosing a liquid sample and the reagents from the reagent supply containers into a measuring cell as well as a measuring transducer for performing optical measurements on the measured liquid accommodated in the measuring cell and formed, for example, by adding the reagents to the liquid sample. The reagents are conveyed via liquid lines formed by hose connections from the reagent containers and transported into the measuring cell. Correspondingly, used measured liquid is transferred, in turn, to a waste container via a hose connection. If the waste container or one or a number of the reagent supply containers must be replaced, attention must be paid that the hose connections are then reconnected correctly. The hoses and conveyor pumps are susceptible to material fatigue and must likewise be subjected to maintenance or be replaced from time to time.

DE 10 2009 029 305 A1 describes an analytical device for automated determining of a measured variable of a liquid sample, which analytical device includes one or a number of liquid containers for one or a number of liquids, e.g. reagents, a measuring cell for accommodating a measured liquid produced by mixing the liquid sample with one or more reagents and a measuring arrangement for providing one or more measurement signals correlated with the measured variable. Furthermore, the analytical device possesses an electronics unit, which includes a control unit for control of the analytical device and for determining the measured variable based on the measurement signals provided by the measuring arrangement, and has a processing unit controlled by the control unit, which processing unit includes a supply and dosing system for supplying and dosing the liquid sample and liquids from the liquid storer into the measuring cell. The analytical device possesses at least one exchangeable cassette, into which the liquid containers and/or at least parts of the processing unit are integrated.

An advantage of this embodiment is that the liquid containers or wear parts of the processing unit, such as hoses or wear parts of the supply and dosing system, which must be renewed by operating personnel from time to time, can be arranged in the cassette. For providing new liquids or for replacing the wear parts, a service person must then only replace the "used" cassette having the liquid containers or wear parts to be replaced with a new cassette.

In the examples of embodiments described in DE 10 2009 029 305 A1, the supply and dosing system includes two peristaltic pumps, wherein a first peristaltic pump serves for selectively supplying and dosing a liquid sample from a sample supply, a cleaning liquid from a liquid container or a calibration standard from another liquid container of the analytical device into the measuring cell. A second peristaltic pump serves for supplying and dosing a reagent into the measuring cell. For selecting, in each case, the liquid to be provided through the first peristaltic pump, valves are provided, which, in each case, are correspondingly operated by the electronic control unit of the analytical device. This construction is relatively simple and permits, for example, the integration of wear parts of the peristaltic pumps in an exchangeable cassette. The supplying of a number of liquids by means of one and the same peristaltic pump only allows a limited processing flexibility, however. In general the dosing precision of peristaltic pumps is inferior to those of piston pumps and can significantly change over the period of use of the hose through material aging. The application of a number of individual valves to be operated is, indeed, basically possible without problem, however, a relatively large installation space is required, depending on how the valves are embodied.

An analytical device for the photometric determination of a parameter of a liquid sample subjected to an oxidizing digestion, e.g. the chemical oxygen demand (COD) or the total nitrogen content, is described in document WO 2005/064328 A1. The device includes a number of liquid containers, from which liquids can be fed into a measuring cell by means of a piston pump connected to all liquid containers. A separate valve is associated with each liquid container. The valve can block the liquid path between each liquid container and the piston pump. Thus, for example, only a single valve can be opened, so that only liquid from the associated liquid container is fed into the cylinder of the piston pump. Alternatively, a number of valves can be opened simultaneously, in order to feed a number of liquids simultaneously. In spite of this, the flexibility of the process guidance of the analysis in this arrangement is limited, since it, indeed, basically permits the simultaneous supplying of a number of liquids, however, it is not possible in this arrangement to set individual feed rates for the different liquids or to dose different volumes of the simultaneously supplied liquids into the measuring cell.

SUMMARY OF THE INVENTION

It is an object of the invention to provide an analytical device of the aforementioned type with a compact and robust construction. The analytical device should permit a high flexibility of the analytical method and be suitable for keeping maintenance for the analytical device to a minimum.

This object is achieved by an analytical device for automated determining of a measured variable of a measured liquid, including:
- a measuring cell for accommodating the measured liquid;
- a measuring transducer for registering a measured value correlating to the measured variable of the measured liquid accommodated in the measuring cell;
- a control unit, which is embodied for determining the measured variable based on the measured value registered by the measuring transducer;
- a system of liquid lines;
- a first liquid container, which is connected to the measuring cell via a first liquid path extending in the system of liquid lines, which first liquid path can be blocked by means of at least a first valve;
- a second liquid container, which is connected to the measuring cell via a second liquid path extending in the system of liquid lines, which second liquid path can be blocked by means of at least a second valve;

wherein a first pump for transport of liquid along the first liquid path is associated with the first liquid container;
and wherein a second pump (different from the first pump) for transport of liquid along the second liquid path is associated with the second liquid container; and
wherein the analytical device has a central valve switching mechanism, especially a valve switching mechanism controllable by the control unit, for actuating the first valve and the second valve.

Since each of the first and the second liquid containers has its own pump for transport of its liquid along a liquid path extending between the respective liquid container and the measuring cell and blockable by at least one valve, individual feed rates can be set for the liquid contained in the first liquid container and for the liquid contained in the second liquid container and/or for dosing individual volumes of the first and, respectively, second liquids into the measuring cell. It is also possible to transport only one of the liquids, or both liquids simultaneously, from the liquid containers into the measuring cell with identical or different feed rates. This leads to a high flexibility in the performing of analytical procedures with the analytical device. The application of a central valve switching mechanism permits a more compact construction and a simplified control in comparison to an arrangement with a number of individually operable valves.

The control unit can include an electronic data processing system, which has at least one microcontroller and one or more data memory circuits, as well as at least a first interface for connecting the control unit to a superordinated unit, for example, a process control system or some other external system, i.e. a data processing system not part of the analytical device. The control unit can be embodied to control the analytical device for the fully automatic performing of analyses and for ascertaining from the measured values registered by the measuring transducer the measured variable to be determined.

In addition to the first and second liquid containers, the analytical device can have a number of other liquid containers for other liquids. All liquid containers of the analytical device can be connected to the measuring cell via the system of liquid carrying lines. The connection of each of the liquid containers to the measuring cell can be formed by an individual liquid path extending through the system of liquid lines and blockable by means of at least one valve. Each path has its own pump for transport of liquid along such. The central valve switching mechanism can be embodied to actuate a number of valves, especially all valves of the analytical device. Furthermore, at least one additional liquid path, which likewise can be blocked by an actuatable valve by the central valve switching mechanism, can be formed in the system of liquid lines; the at least one additional liquid path connects a sample supply (from which the analytical device withdraws the liquid samples to be examined) to the measuring cell. Also this additional liquid path can have its own pump. Alternatively, one of the pumps serving for transport of a liquid from a liquid container into the analytical device can supplementally undertake the supplying of the liquid sample into the measuring cell.

The analytical device can have a basic structure, especially a basic structure formed from individual modules, and, connected to the basic structure, an exchangeable cassette, which includes at least the first and second liquid containers and, in given cases, additional liquid containers of the analytical device. The application of a central valve switching mechanism for actuation of valves serving for blocking liquid paths from the liquid containers to the measuring cell permits an especially compact construction and is, consequently, well suited for such an analytical device having an exchangeable cassette. During operation of the analytical device, the exchangeable cassette is connected to the basic structure via mechanical connecting elements. The cassette can have a housing, which seals the cassette interior from the environment except for one or more connections, via which fluid connections can be formed between the liquid lines or liquid containers within the cassette and liquid lines or liquid containers outside the cassette. Preferably, these connections can be sealed liquid tightly. A fluid connection is here understood to be a structural connection between components, via which structural connection a fluid, preferably a liquid, can be transported from a first component to a second component. Especially, it should not be excluded that additional components in fluid connection are arranged between the first component and the second component. A fluid connection is furthermore especially sealed in such a manner that a loss free transmission of the fluid between the first component and the second component is possible.

An exchangeable cassette is understood to be a cassette, which is connected to the basic structure via one or more connections and is removable from the basic structure and can be replaced with a cassette of the same type. Cassettes of the same type have identical connections, so that each cassette of the same type can be connected to the basic structure without further modifications of the analytical device. Preferably, cassettes of the same type also possess a housing having essentially an identical geometry, especially having essentially identical dimensions. This permits a very simple replacement of at least the liquid containers, since a service person must only replace the cassette without having to directly handle the chemicals contained in the liquid containers. The housings of the basic structure and the exchangeable cassette can be so embodied that the position and orientation of the cassette relative to the basic structure is uniquely fixed. Thus it is assured that the cassette is exclusively located in the position provided for the intended use of the analytical device relative to the components of the analytical device arranged in the basic structure.

The basic structure can especially contain durable, low maintenance and/or expensive components of the analytical device, while the exchangeable cassette preferably contains, besides the liquid containers, also other analytical device components, which are less durable and thus must be replaced from time to time. The basic structure can especially contain the control unit.

The cassette can include at least parts of the first pump and second pump and, in given cases, at least parts of additional pumps. The additional pumps can serve for transport of liquids from additional liquid containers, in given cases, present in the analytical device along, in each case, a liquid path connecting a liquid container to the measuring cell. The pumps can be, for example, peristaltic pumps, membrane pumps or piston pumps.

An advantageous embodiment of the analytical device is one in which the first pump, the second pump and, in given cases present, other pumps of the analytical device are embodied as piston pumps, especially as syringe pumps. The piston pumps can include, in each case, a cylinder and a piston movable in the cylinder, especially a cylinder and a piston of a single use syringe, which are contained within the exchangeable cassette, wherein the basic structure has one or more pump drives, especially one or more linear drives, which are in driving connection with the piston of the pumps when the cassette is connected to the basic structure. The pistons and cylinders contained in the exchangeable cassette can be formed of a low cost material, for example, a synthetic material, e.g. a plastic. The cylinders and pistons of conventional single use syringes have especially proved to be suitable. The exchangeable cassette contains, thus, very cost effective pump parts, which can be simply disposed of after use of the cassette, while the more complex linear drives are arranged outside the cassette in the basic structure. The linear drives can be used over longer periods of time, during which the cassette is replaced multiple times.

The valves can be embodied as multipath valves, such as 3/2 multipath valves, for example, wherein in a first valve position a first liquid path section from the liquid containers to the cylinders of the piston pumps is opened and a second liquid path section from the cylinders of the piston pumps to the measuring cell is blocked, and wherein in a second valve position the first liquid path section from the liquid containers to the cylinders of the piston pumps is blocked and the second liquid path section from the cylinders of the piston pumps to the measuring cell is opened. The first valve position is selected for sucking liquid from a liquid container into the piston pump, while the second valve position is selected for transport of the liquid from the piston pump into the measuring cell. The setting of the respective valve positions of the valves is performed, as mentioned above, by means of the central valve switching mechanism, which is controllable by the control unit.

The cassette includes a processing block, in which at least one part of the system of liquid lines is formed as a channel structure, and includes connections for the liquid tight connection of the channel structure to the liquid containers and connections for the fluid connection of the piston pumps to the channel structure. Preferably, the connections connect the channel structure directly, i.e. without intermediary hoses, to the outputs of the piston pumps and to the measuring cell or to a mixing cell upstream from the measuring cell. In this way, compared to analytical devices known from the state of the art, the number of vulnerable hose lines can be greatly reduced.

The processing block can be formed, for example, of a single, injection molded part. It is also possible to form the processing block from a number of individual components, for example, plates placed in contact with one another, in which plates channels are formed in their planes and/or perpendicular to their planes so that a three dimensional channel structure forming liquid lines arises upon placing the plates in contact with one another.

The cassette can furthermore have a valve block, which includes the first valve and second valve and, present in given cases, additional valves for blocking or opening liquid paths formed in the system of liquid lines, wherein the valves are embodied as multipath valves, especially as 3/2 multipath valves.

The multipath valves can have, in each case, a hollow space formed in the valve block; the hollow space is formed as a liquid tight cavity in a lateral surface of the valve block covered by a flexible wall, especially an elastic, deformable wall, especially an elastic, deformable membrane, and a number of liquid lines open into the hollow space, which liquid lines are embodied as channels extending within the valve block, wherein at least one of the multipath valves includes one or more blocking members applied on the flexible wall, wherein each blocking member is displaceable in a movement direction, which has at least one component extending perpendicularly to the flexible wall for the actuation of the multipath valve in order to block one of the liquid lines opening into the hollow space from the other liquid lines opening into the hollow space by deforming the flexible wall. In such case, the opening can serve as a valve seat for at least one of the liquid lines opening into the hollow space; the blocking member presses the flexible wall against the valve seat for blocking the liquid line.

The valve block can be connected to the processing block, in which at least one part of the system of liquid lines is formed as a channel structure, in such a manner that the multipath valves formed in the valve block interact with the liquid lines formed in the processing block to block and/or open the liquid lines. For example, the processing block and the valve block can be formed by a one piece injection molded part. The valve block and the processing block can also be two separate components, which are releasably connected to one another via connections. Like the processing block, the valve block can be composed of a number of mutually adjoining components and/or components joined to one another, for example, a number of mutually adjoining plates.

The central switching mechanism can shift the blocking members electrically, pneumatically, mechanically or in another manner and so actuate the valves. The blocking members can be embodied, for example, as seated pins or plugs movable in an axial direction, which are moved by means of corresponding linear drives. In an embodiment, the central switching mechanism can include a rotatable shaft, which has cams or cavities, which interact with the blocking members of the valves in order to open or block the liquid paths blockable by the valves. The shaft in this embodiment can contact the blocking members in such a manner that in the case of a rotational movement of the shaft around its own axis the cavities or cams of the shaft compel a movement of the blocking members against the flexible wall or permit a movement of the blocking members in the direction pointing away from the flexible wall.

The valve block and parts of the central switching mechanism can be components of the exchangeable cassette. If the switching mechanism, for example, has a rotatable shaft with cavities or cams for actuation of the blocking members, the shaft can be a component of the cassette. In this case, the basic structure can have a drive controllable by the control unit; the drive is in active contact with components of the central switching mechanism, for example, a rotatable shaft, that are contained in the cassette, when the cassette is connected to the basic structure. In this way, the relatively complex but highly wear resistant drive can remain in the basic structure while the wear susceptible valves and mechanical components of the switching mechanism can be replaced and renewed regularly with the exchangeable cassette.

The cassette can contain a data memory, which is embodied to store data of the cassette, information on the liquid containers contained in the cassette and/or on the liquids contained in the liquid containers, especially on the amount of liquid contained in the liquid containers, wherein the control unit is embodied to store data in the data memory and/or to read out data from the data memory when the cassette is connected to the basic structure. For this, the control unit can have an additional interface, which is connected to a complementary interface of the data memory with the connection of the exchangeable cassette to the basic structure. The data memory contained in the cassette can be a component of a microcomputer, which includes at least one microcontroller in addition to the data memory.

In an embodiment, the cassette can have a connection for the connection of the part of the system of liquid lines contained in the cassette to the measuring cell contained in the basic structure. In this embodiment the measuring transducer and the measuring cell are thus contained in the basic structure outside the cassette, wherein the measuring transducer is arranged relative to the measuring cell so that the measuring transducer, for registering measured values, is in contact with a measured liquid contained in the measuring cell.

Alternatively, the measuring cell can, however, also be a component of the cassette. In this embodiment, it is possible to accommodate all liquid contacting components of the analytical device in the cassette. If the exchangeable cassette is connected to the basic structure, the measuring transducer arranged in the basic structure is in contact with a measured liquid contained in the measuring cell for registering the measured value.

If the measuring transducer is, for example, an optical sensor having a radiation source emitting measuring radiation and a receiver, which outputs a measurement signal dependent on the radiation intensity incoming on a sensitive surface of the receiver, the measuring transducer is brought into contact with the measured liquid, in that radiation emitted by the radiation source is radiated on a radiation path extending through the measured liquid between the radiation source and the receiver, especially extending through the wall or through one or more windows of the measuring cell. If the measuring transducer is embodied as an amperometric or potentiometric sensor, e.g. as an ion selective electrode or conductivity sensor, the measuring transducer is brought into contact with the measured liquid in that an immersion region of the measuring transducer designed for contact with the measured liquid is wetted by the measured liquid. For example, the measuring transducer, or at least the immersion region of the measuring transducer, can be arranged within the measuring cell for this purpose.

The registering of a measured value by the measuring transducer can be triggered by the control unit. The determining of the measured variable from the measured value likewise occurs through the control unit.

The liquid containers can be embodied as flexible reagent bags having, in each case, a connection, especially a single connection, for the connection of the reagent bag to a liquid line, in each case. A liquid reagent can be removed from a flexible reagent bag without the need for a pressure equalization within the liquid container. Thus, only a single container opening, namely the aforementioned connection for the connection of the reagent bag to a liquid line, is required for the removal of liquid so that the penetration of air, especially oxygen or other reactive gases, into the liquid containers can be substantially suppressed.

The liquid containers, especially liquid containers embodied as flexible reagent bags, can advantageously have a container wall impermeable to visible light and/or UV radiation. Therewith, photochemical or aging or decomposition processes, which are accelerated by radiation, of the liquid contained therein are at least slowed or even suppressed. With an embodiment of the liquid containers as reagent bags, the container wall can be formed, for example, by a film impermeable to visible light and/or UV radiation. Especially advantageous in this context are films or coatings, which supplementally reflect IR radiation and thus also thermally insulate the pouch content.

In an embodiment, a temperature control apparatus, especially a cooling apparatus, which, for example, includes a Peltier element, can be associated with at least one of the liquid containers.

If the liquid containers are embodied as reagent bags, they can be arranged in support containers, which have a floor and fixed walls surrounding the reagent bag laterally, in the analytical device, especially within the exchangeable cassette. The temperature control apparatus can be arranged, for example, within the support container or integrated in at least one container wall of the support container. The container walls and the floor of the support container can have thermal insulation. For example, the container walls and the floor can have a double walled structure.

BRIEF DESCRIPTION OF THE DRAWINGS

The invention will now be explained in greater detail based on the examples of embodiments illustrated in the drawings. The figures of the drawing show as follows.

DETAILED DESCRIPTION IN CONJUNCTION WITH THE DRAWINGS

Figure 1:
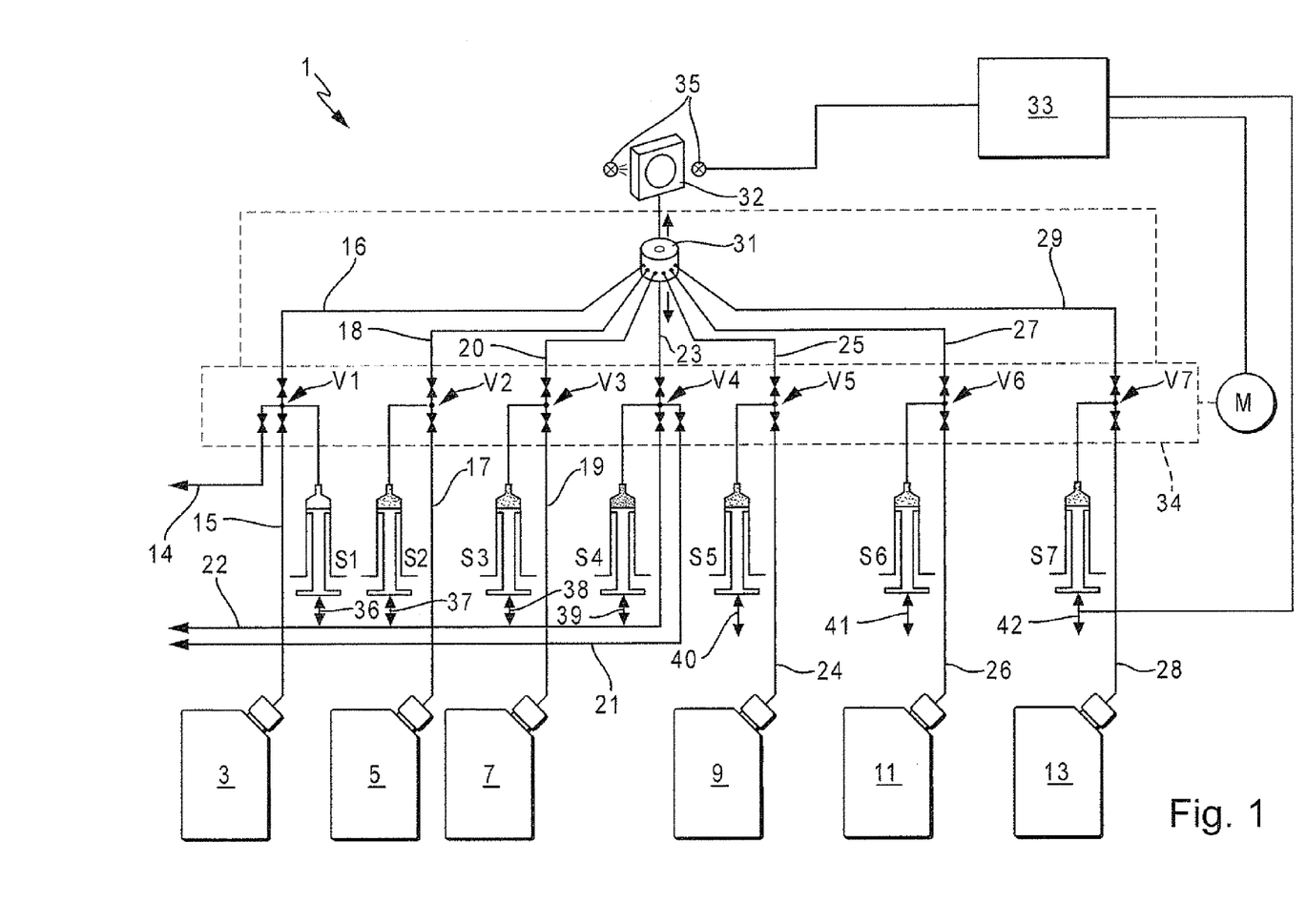
FIG. 1 is a schematic representation of an analytical device.

FIG. 1 shows a schematic representation of an analytical device 1 having a number of liquid containers 3, 5, 7, 9, 11 and 13 and a system of liquid line 14-29, via which the liquid containers 3, 5, 7, 9, 11 and 13 are connected to a measuring cell 32 via a mixing cell 31. The liquid paths extending through the system of liquid lines from the liquid containers 3, 5, 6, 9, 11 and 13 to measuring cell 32 are blockable, in each case by at least one multipath valve V1, V2, V3, V4, V5, V6, V7. All valves V1, V2, V3, V4, V5, V6 and W are actuatable by means of a central switching mechanism 34. The transport of liquid along the liquid paths formed in the system of liquid lines occurs by means of a row of piston pumps S1, S2, S3, S4, S5, S6 and S7.

Analytical device 1 can be operated completely automatically. For this, it includes a control unit 33, which provides both the functions of an evaluating unit for determining the measured variable as well as the functions of a control unit for control of the method performed in the analytical device in the example shown here. Control unit 33 includes a data processing system, for example, a computer or a measurement transmitter, having at least one processor and one or more data memories. Control unit 33 can also have an input apparatus for the input of commands or parameters by a service person and/or an interface for the receipt of commands, parameters or other data from a superordinated unit, for example, a process control system. Furthermore, control unit 33 can also have an output apparatus for the output of data, especially measurement results or operating information, to a user or an interface for the output of data to the superordinated unit. Control unit 33 can also be realized through a number of data processing units, which are especially spatially distributed and in contact with one another for communication.

Control unit 33 is connected to pump drives 36-42 (in FIG. 1, only the connection to drive 42 is presented, by way of example) of piston pumps S1, S2, S3, 54, S5, S6 and S7 and with a drive M of central switching mechanism 34, in order to transport liquids into mixing cell 31 and from there further into measuring cell 32, or out of measuring cell 32. Control unit 33 is connected, moreover, to an optical measuring transducer 35, which includes an optical transmitter and an optical receiver, in order to control measuring transducer 35, on the one hand, and to ascertain the measured variable to be determined from the measurement signals of receiver 35, on the other hand. The optical transmitter can comprise, for example, one or more light emitting diodes (LEDs), especially a number of LEDs, which emit light of different wavelengths in each case. The receiver can have one or more photoelectric elements, especially one or more photodiodes.

Analytical device 1 furthermore includes a liquid line 14 for supplying a liquid sample from a sample supply (not illustrated). Liquid line 14 for the liquid sample is connected to mixing cell 31 via another liquid line 16. Control unit 33 conveys the liquid sample for pretreating in mixing cell 31 by correspondingly operating pump drive 36 and operating central switching mechanism 34 by means of the drive M for actuation of valve V1.

In the present example the measured variable to be determined by the analytical device is an analyte concentration in the liquid sample. Analytical device 1 includes three liquid containers 9, 11, and 13, which contain reagents, which are mixed with the liquid sample simultaneously or one after the other in order to bring about a change in the liquid sample, for example, a coloring or a color change, which is photometrically detectable by measuring transducer 35, by means of a chemical reaction with an analyte contained in the sample. The reagents can be dosed into mixing cell 31 by control unit 33 by actuating pump drives 40, 41, 42 in combination with valves V5, V6 and V7 and be mixed with the liquid sample there. For the photometric determination of the analyte concentration the measured liquid produced by mixing the liquid sample with the reagents can be further transported into measuring cell 32. Measuring cell 32 includes optical windows, which are porous to the measuring radiation emitted by the optical transmitter. The radiation transmitted from the measured liquid is received by the receiver of optical measuring transducer 35, which outputs a measurement signal correlated to the intensity of the transmitted radiation to control unit 33. Control unit 33 is embodied to derive and store a measured value of the measured variable to be determined, here the analyte concentration, from the measurement signal and/or to output the measured value via a user interface or to a superordinated unit.

Furthermore, analytical device 1 has three additional supply containers 3, 5 and 7 available. Supply container 3, which is connected to the mixing cell via the same liquid line 16 as liquid line 14, via which the liquid sample of the sample supply is removed, contains a cleaning solution. The two additional supply containers 5 and 7 contain, in each case, a standard solution, for example, a standard solution with a known concentration of the analytes in the one supply container 5 and analyte free water, especially distilled water in the other supply container 7. By means of piston pumps S1, S2 and S3 in combination with valves V1, V2 and V3, these liquids can routed by the control unit into mixing cell 31 via liquid lines 15, 16, 17, 18, 19 and 20 and be conveyed further into measuring cell 32.

Mixing cell 31 is connected to a waste container (not illustrated) via a liquid path extending through liquid lines 23 and 21; the liquid path can be blocked by means of valve V4. Pump S4 serves to transport used measured liquid from measuring cell 32 to the waste container via mixing cell 31 and liquid lines 23 and 21.

Liquid containers 3, 5, 7, 9, 11, 13, parts of piston pumps S1, S2, S3, S4, S5, S6, 57, at least one part of the system of liquid lines and mixing cell 31 can be arranged in an exchangeable cassette, which can be releasably connected to a basic structure. The basic structure includes the additional components of analytical device 1, for example, measuring cell 32, measuring transducer 35, control unit 33, pump drives 36, 37, 38, 39, 40, 41, 42 of piston pumps S1, S2, S3, S4, S5, 56, S7, drive M of central switching mechanism 34 and, in given cases, other components, such as e.g. a ventilation system and/or a cooling system for the analytical device. The basic structure can be formed as a single piece or from a number of modules, especially modules releasably connected to one another.

Figure 2:
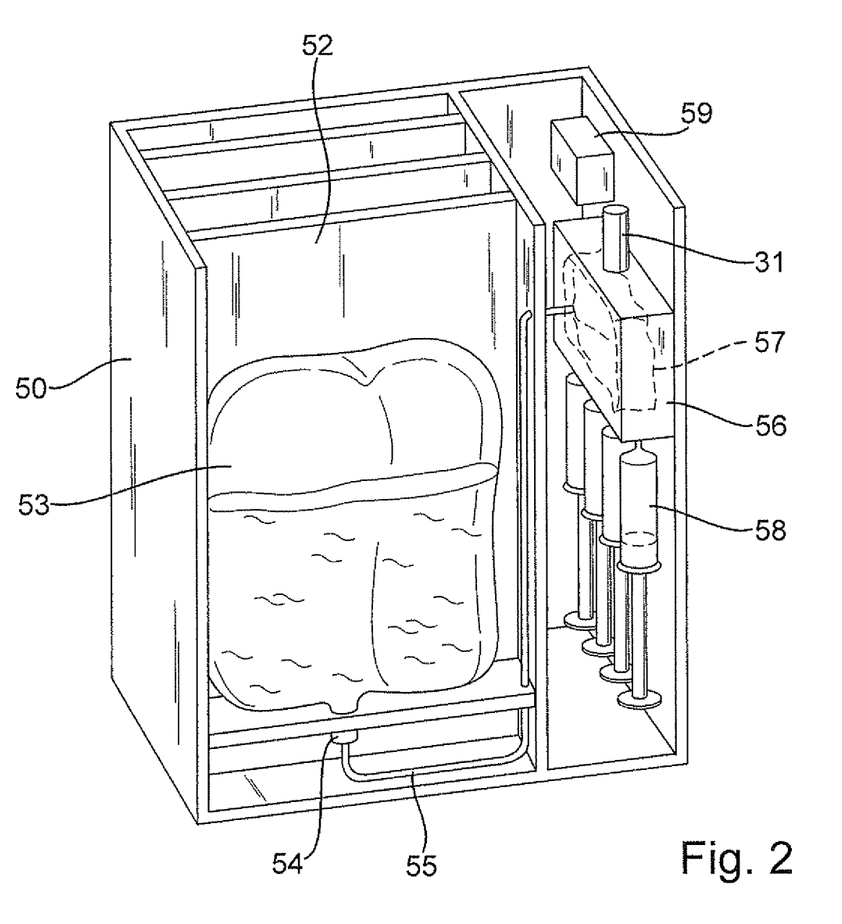
FIG. 2 is a schematic section representation of an exchangeable cassette of an analytical device according to the schematic representation in FIG. 1.

An example of an exchangeable cassette 50 is schematically shown in FIG. 2. In the example shown here, the liquid containers contained in the cassette are embodied as reagent bags 53 having a flexible wall; reagent bags 53 are contained in a support structure 52 formed within cassette 50. However, the liquid containers can also be embodied as conventional containers having a solid wall. Reagent bag 53 shown here includes a wall impermeable to visible light and/or UV radiation in order to slow or suppress photochemical decomposition processes or decomposition processes accelerated by radiation; the decomposition processes can take place in the liquid contained in reagent bag 53. For lengthening the storage life of the liquid contained in reagent bags 53, the cassette 50 can include a temperature control apparatus, especially a cooling system, for the reagent bag. The temperature control apparatus can include, for example, Peltier elements, which are placed on one or more walls of support structure 52 (not shown here).

Reagent bag 53 includes a connection 54 connected to a liquid line 55; the liquid is suppliable via connection 54 to the system of liquid lines, which in the example shown here is embodied as a channel structure 57 formed in a processing block 56. Processing block 56 can be formed by one or more components secured to one another; for example, the components are manufactured using injection molding technology. The channel structure 57 forms the liquid lines 14-29 shown in FIG. 1, so that the liquid paths extend through channel structure 57 between the liquid containers 53 contained in cassette 50 and mixing cell 31. Processing block 56 includes connections for a number of piston pumps 58 on one side and a connection to mixing cell 31 on another side, here the side lying oppositely. The number of liquid lines formed by hoses in this embodiment is greatly reduced compared to analytical devices known from the state of the art. Since hose connections are susceptible to aging phenomena and defects, the functional stability of the analytical device is significantly improved and the maintenance effort is reduced. Moreover, the risk that hose connections are switched in the case of an intervention in cassette 50 by a maintenance person is lessened.

Piston pumps 58 have, in each case, a cylinder and an axially movable piston in the cylinder for sucking liquid into the cylinder or for ejecting liquid from the cylinder. It has been found that a piston pump 58 with sufficient dosing accuracy can be formed by a cylinder and piston of a conventional single use syringe, especially made from synthetic material, using an annular seal, which is secured in a peripheral cavity of the piston and slides in the cylinder in the case of movement of the piston and is created from a chemically inert sealing material for sealing the cylinder interior serving for accommodating the liquid. Each piston pump 58 can be actuated by means of its own pump drive (see pump drives 36-42 in FIG. 1). The pump drives are embodied as linear drives and arranged in the basic structure outside exchangeable cassette 50. In the case of connecting cassette 50 to the basic structure, the piston or connecting elements connected to the piston engage a movable component, for example, a slide, of the linear drives.

Exchangeable cassette 50 furthermore includes an electronics unit 59, which includes at least one data memory. In an alternative embodiment electronics unit 59 can also be embodied as a microcomputer having at least one microprocessor and a data memory. Electronics unit 59 includes an interface, via which electronics unit 59 is connectable to control unit 33, which is accommodated in the basic structure, for data exchange and for the supply of energy to electronics unit 59 by control unit 33. Information concerning cassette 50 or the liquids contained in the liquid containers of cassette 50 can be stored in the data memory of electronics unit 59. Possible information about the liquids stored in the data memory can be chemical composition, an expiration date or the liquid amount contained in the liquid containers. Control unit 33 can read out data from the data memory and write data in the data memory. For example, control unit 33 can read out the current liquid amount contained in liquid containers 53 from the data memory and monitor the consumption of the individual liquids during the analytical operation and, based on the liquid consumption recorded by control unit 33, write updated values of the liquid amounts still contained in liquid containers 53 in the data memory from time to time.

Moreover, sensors, which monitor the fill level of liquid containers 53 or a temperature reigning in cassette 50 can be contained in cassette 50. The sensor measured values can be registered and/or stored by electronics unit 59 and be taken into consideration for diagnostic purposes. Based on a temperature profile registered by a temperature sensor, a microcomputer possibly present in electronics unit 59 or the superordinated control unit 33 of analytical device 1 connected to electronics unit 59 can derive a time span corresponding to the shelf life of the liquids. This time span is longer in the case of low temperatures, in which decomposition reactions run slower, than in the case of high temperatures. Since the temperature curve and/or other measured variables influencing the storability of the liquids are registered and stored in the data memory of electronics unit 59 of cassette 50, a data history, such as e.g. the time periods, in which the liquids were exposed to elevated temperatures, registered over the duration of the operation of cassette 50 can be taken into consideration in the ascertaining of the remaining shelf life of the liquids.

Valves are arranged on one side of processing block 56, in which channel structure 57 forms a part of the liquid lines; by means of these valves, the liquid paths extending between the liquid containers and the sample supply are blockable (not shown in FIG. 2). The valves can be formed in processing block 56 or in a valve block, especially a releasably connected valve block, connected to the processing block.

Figure 3A:
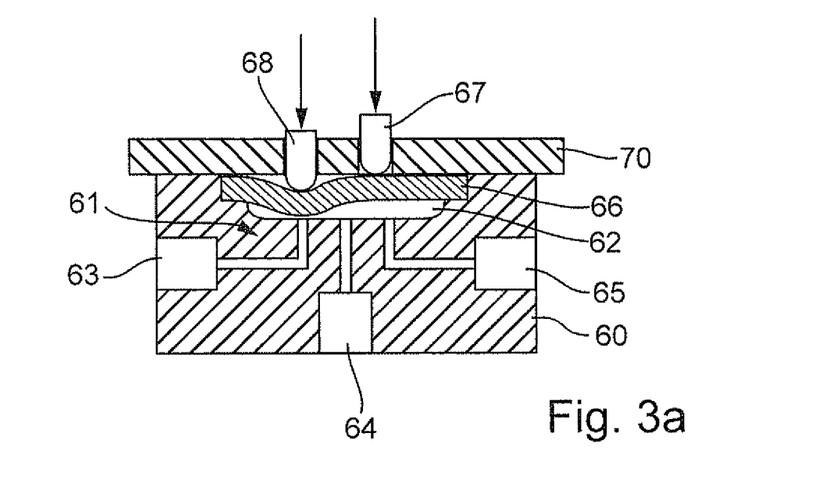
FIG. 3*a* is a schematic section representation of a valve block, wherein the section extends through one of the valves.

FIG. 3a shows a schematic sectional illustration of such a valve block 60. Valve block 60 is connectable to processing block 56 shown in FIG. 2 in such a manner that liquid paths extending through channel structure 57 between liquid containers 3 and mixing cell 31 are blockable or unblockable by means of the valves formed in valve block 60. FIG. 3a shows a section through one of the valves formed in valve block 60.

The valve 61 shown in the section is formed by a hollow space 62, into which three liquid lines 63, 64, 65 open. Hollow space 62 is covered and sealed liquid tight by a sealing plate 66, which is made from a flexible material and can also be embodied as a thin sealing membrane. Two blocking members 67, 68 abut sealing plate 66; blocking members 67, 68 are movable through a holding plate 70 in a direction perpendicular to sealing plate 66. Each blocking member 67, 68 is arranged lying opposite an opening of one of liquid lines 63, 65. For the blocking of one of these liquid lines 63, 65 against the two other liquid lines opening into hollow space 62, blocking member 67 or 68 can be shifted in an axial direction against sealing plate 66 so that sealing plate 66 is deformed and pressed by blocking member 67, or 68 against the opening of the liquid line 63 or 65 lying oppositely, so that the opening serving as a valve seat in this way is sealed liquid tight.

A central valve switching mechanism arranged in the basic structure outside exchangeable cassette 50 is provided for the actuation of the valves. In the example shown here, the switching mechanism includes one or more actuators (indicated by arrows in FIG. 3a), which exert an axially acting force on blocking members 67, 68 for blocking a liquid path. An opening of the liquid path occurs, in that the actuators exert no axially acting force on the corresponding blocking member 67, 68, so that the blocking member 67, 68 is shifted in an axial direction away from the valve seat formed by the opening of the liquid line and the liquid line is again opened due to the return force of the deformable sealing plate 66 or due to a liquid pressure within hollow space 62. Alternatively, the actuators can also be embodied to actively move blocking members 67 or 68 in the direction facing away from the sealing plate, in order to unblock the opening of the associated liquid line 63 or 65.

Liquid line 63 can be connected to a liquid container of the analytical device, for example, via the channel structure formed in the processing block. Liquid line 64 can be connected in an equal manner to a piston pump via the channel structure formed in the processing block. Liquid line 65 can be connected to mixing cell 31 of the analytical device. In a first valve position, in which the first blocking member 67 presses sealing plate 66 against the opening of liquid line 65 but second blocking member 68 only abuts sealing plate 66 without any additional force, a first liquid path section, which extends from the liquid containers to the cylinder of the piston pump via liquid line 63 and liquid line 64, is opened and the piston pump can pull the liquid from the liquid containers. In a second valve position, which is shown in FIG. 3, in which first blocking member 67 only abuts sealing plate 66 without any additional force action and second blocking member 68 presses the sealing plate against the opening of liquid line 63, the first liquid path section is blocked, but a second liquid path section, which extends from the piston pump into mixing cell 31 via liquid line 64 and liquid line 65, is opened. The piston pump can thus dose the liquid contained in its cylinder into the measuring cell via the opened second liquid path section. Furthermore, there is a third valve position, in which the two blocking members 67, 68 close the oppositely lying openings of liquid lines 63 and 65 by pressing on sealing plate 66. In this position both liquid path sections are blocked. Valve block 60 can include a number of such valves, and so form an arrangement as shown schematically in FIG. 1 in combination with the piston pumps in cassette 50 and the liquid lines formed in the processing block.

The central valve switching mechanism can shift the blocking members electrically, pneumatically, mechanically or in another manner and so actuate the valves. The blocking members can be embodied, for example, as stamps movable in an axial direction, which stamps are moved by means of corresponding linear drives or other pressure or force providers.

Figure 3B:
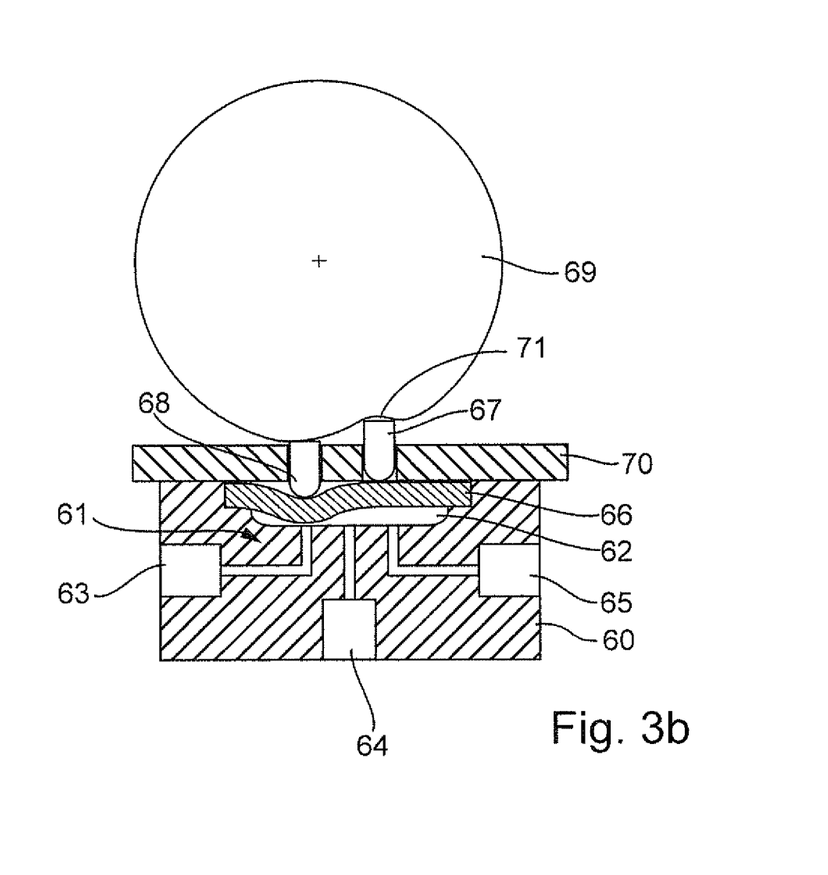
FIG. 3*b* is a schematic section representation of the valve block illustrated in FIG. 3*a* having a shaft of a central valve switching mechanism for actuation of the valves.

In an advantageous embodiment according to FIG. 3b, the central valve switching mechanism includes a rotatable shaft 69, which has cavities, which interact with the blocking members of the valves formed in the valve block in order to open the liquid paths blockable by the valves. In this variant the valves are closed in the unactuated state, i.e. both blocking members 67, 68 of valve 61 press sealing plate 66 against the valve seats formed by the openings of liquid lines 63, 65 so that valve 61, which was described in more detail above, for example, is located in its third valve position in the unactuated state. Through rotation of shaft 69, a cavity 71 in shaft 69 can interact with the first or second blocking member 67, 68 in such a manner that, in each case, one of liquid lines 64 or 65 is opened, in order to switch valve 61 to its first or second valve position.

In an alternative embodiment the shaft can also have cams, which interact with the blocking members in order to block the liquid paths. The central valve switching mechanism can at least partially be a component of exchangeable cassette 50. The drive of the central switching mechanism, for example, a drive of rotatable shaft 69, is preferably arranged in the basic structure. In this embodiment, all valves of valve block 60 actuatable by means of shaft 69 are arranged in an axial direction with reference to the axis of shaft 69, i.e. perpendicular to the plane of the drawing of FIG. 3b. In this way, shaft 69 can actuate all valves in the manner described.

In the following, the operation sequence of an analytical method performed by the analytical device for determining an analyte concentration in a liquid sample will now be described based on FIG. 1:

To begin an analytical cycle the liquid sample is transported along a first liquid path along liquid lines 14 and 16 into mixing cell 31. The valve position of the valve V1 is set by means of central switching mechanism 34 controlled by control unit 33 so that a first liquid path section from the sample supply to the piston pump S1 is opened, while a second liquid path section from piston pump S1 to mixing cell 31 is blocked. An additional liquid path from liquid containers 3 containing a cleaning liquid to the piston pump via liquid line 15 is also blocked in this valve position. After this, a predetermined liquid amount is conveyed into piston pump S1 by control unit 33 through a corresponding control of pump drive 36, valve V1 is switched to a second valve position, in which the second liquid path section is opened, while the first liquid path section is blocked and the liquid path to liquid containers 3 containing the cleaning liquid is likewise blocked. The control unit then controls pump drive 36 in a suitable manner to dose a predetermined amount of the liquid sample into mixing cell 31.

Reagents from liquid containers 9, 11 and 13 can be dosed into mixing cell 31 simultaneously or sequentially. For this, the valves V5, V6 and V7 are switched to a first valve position, in which each first liquid path section from liquid containers 9, 11 and 13 to the cylinders of piston pumps S5, S6 and S7 via liquid lines 24, 26 and 28 is opened, while the second liquid path section from piston pumps S5, S6 and S7 to mixing cell 31 via the liquid lines 25, 27 and 29 is blocked. In the case of this position of valves V5, V6 and V7, piston pumps S5, S6, S7 can, in each case, suck a liquid amount predetermined by control unit 33 into its cylinder. Thereafter valves V5, V6 and V7 are switched to a second valve position, in which the second liquid path section is opened and the first liquid path section is blocked. The control unit can then actuate the pump drives 40, 41 and 42 for dosing, in each case, the desired amount of the reagents into mixing cell 31. Since an individual piston pump having an individual pump drive is associated with each reagent, each reagent can be transported into mixing cell 31 at a different feed rate and/or with a variable volume.

The reagents are mixed with the liquid sample in mixing cell for forming a measured liquid. If the liquid sample contains the analyte, whose concentration is to be determined, in such case, a chemical reaction occurs, which affects a photometrically detectable change. By means of piston pump S1, the measured liquid is further transported to measuring cell 32, where optical measuring transducer 35 registers a measurement signal, which is dependent on the analyte concentration to be determined. Control unit 33 receives the registered measurement signal from measuring transducer 35 and derives the analyte concentration present in the liquid sample therefrom. After terminating the measuring, measuring cell 32 is emptied, in that by means of valve V4 a liquid path from measuring cell 32 via mixing cell 31 and liquid line 23 to piston pump S4 is opened, and piston pump S4 is actuated in order to suck the used measured liquid out the measuring cell 32. After switching valve V4 to a second valve position, in which the liquid path between measuring cell 32 and piston pump S4 is blocked and a liquid path from piston pump 54 via liquid line 21 to a waste container is opened, the used measured liquid is then transported from piston pump S4 to the waste container. The analytical cycle is ended therewith.

The analytical cycle can contain, moreover, a zero line measuring, in which a liquid sample is conveyed into the measuring cell 32 by means of piston pump S1 in an analogous manner as described above, without, however, adding reagents from containers 9, 11 or 13. By means of measuring transducer a zero signal can be ascertained for the liquid sample contained in the measuring cell; the value of the zero signal is stored by control unit 33, and is taken into consideration in determining the measured value of the analyte concentration of a measured liquid formed by mixing a liquid sample with the reagents.

Analytical device 1 can repeatedly perform such an analytical cycle. Moreover, a cleaning step can be performed between individual analytical cycles or after performing a series of analytical cycles; in the cleaning step, a cleaning liquid is conveyed from container 3 into mixing cell 31 and further into measuring cell 32 by means of piston pump S1, which also serves for supplying the liquid sample into mixing cell 31 in the example shown here, and sucked back out and emptied into a waste container by means of piston pump S4. The liquid transport occurs, as described in detail for the measuring cycle, by actuating pump drives 36 and 39 and through a corresponding switching of valves V1 and V4 by means of central switching mechanism 34.

At predetermined time intervals, for example, after a predetermined number of analytical cycles or before performing each analytical cycle, one or more calibration measurements can be performed, in which, instead of a liquid sample from the sample supply, a standard solution from liquid containers 5 and/or 7 is conveyed into mixing cell 31 by means of piston pumps S2 and/or S3 and the corresponding valves V2 and V3 actuated by the central switching mechanism in an analogous manner as for the supplying of reagents from containers 9, 11 and 13 described above. The operational sequence of a calibration measurement occurs, moreover, in the same manner as an analytical cycle using a liquid sample from the sample supply.

The invention claimed is:

1. An analytical device for automated determining of a measured variable of a measured liquid, comprising:
    a measuring cell for accommodating the measured liquid;
    a measuring transducer for registering a measured value correlating to the measured variable of the measured liquid contained in said measuring cell;
    a control unit, which is embodied for determining the measured variable based on the measured value registered by said measuring transducer;
    a system of liquid lines;
    a first liquid container, which is connected to said measuring cell via a first liquid path extending in the system of liquid lines, which first liquid path can be blocked by means of at least a first valve; and
    a second liquid container, which is connected to said measuring cell via a second liquid path extending in the system of liquid lines, which second liquid path can be blocked by means of at least a second valve, wherein:
    a first pump for transport of liquid along the first liquid path is associated with the first liquid container;
    a second pump (different from the first pump) for transport of liquid along the second liquid path is associated with the second liquid container; and
    the analytical device comprises a central valve switching mechanism controllable by said control unit, for actuating the first valve and the second valve.

2. The analytical device as claimed in claim 1, wherein:
    other liquid paths, which, in each case, are blockable by means of at least one valve, are formed in the system of liquid lines; to which liquid paths is associated, in each case, its own pump, which is different from the first pump and second pump, for transport of liquid along the respective liquid path; and
    said central valve switching mechanism is embodied to actuate all valves, which are embodied for blocking the additional liquid paths, of the analytical device.

3. The analytical device as claimed in claim 1, wherein:
    the analytical device comprises a basic structure, and an exchangeable cassette connected to the basic structure, and said exchangeable cassette includes at least the first and second liquid containers.

4. The analytical device as claimed in claim 3, wherein:
    said cassette includes at least parts of the first pump and the second pump and at least parts of additional pumps associated to the other liquid paths blockable by at least one valve.

5. The analytical device as claimed in claim 3, wherein:
    the first pump, the second pump and, the additional pumps of the analytical device are embodied as piston pumps.

6. The analytical device as claimed in claim 5, wherein:
    said piston pumps include, in each case, a cylinder and a movable piston in the cylinder, which are contained in said exchangeable cassette; and
    the basic structure comprises one or more pump drives, which are in driving connection with the pistons of the pumps when the cassette is connected to the basic structure.

7. The analytical device as claimed in claim 5, wherein:
    the valves are embodied as multipath valves, wherein, in a first valve position, a first liquid path section from the liquid containers to the cylinders of said piston pumps is opened and a second liquid path section from said piston pumps to said measuring cell is blocked; and
    in a second valve position, the first liquid path section from the liquid containers to said piston pumps is blocked and the second liquid path section from said piston pumps to said measuring cell is opened.

8. The analytical device as claimed in claim 5, wherein:
    said cassette comprises a processing block, in which at least a part of the system of liquid lines is formed as a channel structure and comprises connections for a liquid tight connection of said channel structure to the liquid containers and connections for liquid tight connection of said piston pumps to the channel structure.

9. The analytical device as claimed in claim 8, wherein:
    said cassette comprises a valve block, which includes the first valve and second valve and additional valves for blocking other liquid paths formed in the system of liquid lines present in the valve block; and
    the valves are embodied as multipath valves.

10. The analytical device as claimed in claim 9, wherein:
    the multipath valves, in each case, comprises a hollow space formed in the valve block, which hollow space is formed as a cavity in a lateral surface of the valve block covered liquid tightly by a flexible wall, and into which hollow space a number of liquid lines open, which are embodied as channels extending within said valve block; and
    at least one of said multipath valves includes one or more blocking members applied on said flexible wall, each blocking member for actuation of said multipath valves is displaceable in a movement direction, which has at least one component extending perpendicularly to said flexible wall, in order to block at least one of the liquid lines opening into the hollow space from the other liquid lines opening into the hollow space by deforming said flexible wall.

11. The analytical device as claimed in claim 9, wherein:
    said valve block is connected, especially releasably connected, to said processing block, in which at least one part of the system of liquid lines is formed as a channel structure in such a manner that said multipath valves formed in said valve block interact with the liquid lines formed in said processing block for the blocking and/or opening of said liquid lines.

12. The analytical device as claimed in claim 10, wherein:
    said central valve switching mechanism includes a rotatable shaft, which comprises cams or cavities, which interact with the blocking members of said multipath valves, in order to open or block the liquid paths blockable by said multipath valves.

13. The analytical device as claimed in claim 12, wherein:
the basic structure comprises a drive controllable by the control unit; said drive is releasably connected with the rotatable shaft when said cassette is connected to said basic structure.

14. The analytical device as claimed in claim 3, wherein:
said cassette contains a data memory, which is embodied to store data of said cassette, information on the liquid containers contained in said cassette and/or on the liquids contained in the liquid containers, especially the fill level or the liquid amount in the liquid containers contained in said cassette; and
said control unit is embodied to store data in the data memory and/or read out data from the data memory when said cassette is connected to the basic structure.

15. The analytical device as claimed in claim 3, wherein:
said cassette comprises a connection for the connection of the part of the system of liquid lines contained in said cassette to said measuring cell contained in the basic structure.

16. The analytical device as claimed in claim 3, wherein:
the basic structure is formed from individual modules.

17. The analytical device as claimed in claim 3, wherein:
said exchangeable cassette includes additional liquid containers of the analytical device.

18. The analytical device as claimed in claim 1, wherein:
other liquid paths, which, in each case, are blockable by means of at least one valve, are formed in the system of liquid lines; and
the analytical device further comprises additional pumps different from the first pump and second pump, wherein:
to the other liquid paths is associated, in each case, one of said additional pumps for transport of liquid along the respective liquid path; and
wherein the central valve switching mechanism is embodied to actuate all valves, which are embodied for blocking the additional liquid paths.

19. The analytical device as claimed in claim 18, wherein:
the first pump, the second pump and the additional pumps are embodied as piston pumps.

20. The analytical device as claimed in claim 19, further comprising:
a processing block, in which at least a part of the system of liquid lines is formed as a channel structure and comprises connections for a liquid tight connection of said channel structure to the liquid containers and connections for liquid tight connection of said piston pumps to the channel structure.

21. The analytical device as claimed in claim 20, further comprising:
a valve block, which includes the first valve and second valve, and additional valves for blocking other liquid paths formed in the system of liquid lines present in the valve block, wherein the valves are embodied as multipath valves; and wherein:
said valve block is connected to the processing block in such a manner that said multipath valves formed in said valve block interact with the liquid lines formed in the processing block to block and/or open the liquid lines.

* * * * *